United States Patent [19]
Angerbauer et al.

[11] Patent Number: 5,409,910
[45] Date of Patent: Apr. 25, 1995

[54] SUBSTITUTED PYRIDINES

[75] Inventors: Rolf Angerbauer; Peter Fey; Walter Hübsch, all of Wuppertal; Thomas Philipps, Cologne; Hilmar Bischoff, Wuppertal; Hans-Peter Krause, Schwelm; Jörg P. von Gehr, Bochum; Delf Schmidt, Wuppertal, all of Germany

[73] Assignee: Bayer Aktiengesellschaft, Leverkusen, Germany

[21] Appl. No.: 169,804

[22] Filed: Dec. 17, 1993

[30] Foreign Application Priority Data

Dec. 24, 1992 [DE] Germany .................. 42 44 029.7

[51] Int. Cl.$^6$ .................. A61K 31/675; C07D 401/00
[52] U.S. Cl. ................. 514/89; 514/318; 514/336; 514/340; 514/352; 546/24; 546/281; 546/283; 546/305; 546/312; 546/330; 546/339; 546/340
[58] Field of Search ........... 546/339, 340, 24, 281, 546/283, 305, 312, 330; 514/277, 89, 318, 352, 336, 340

[56] References Cited

U.S. PATENT DOCUMENTS

| | | | |
|---|---|---|---|
| 4,231,938 | 11/1980 | Monaghan et al. | 549/292 |
| 4,925,852 | 5/1990 | Kessler et al. | 514/333 |
| 5,006,530 | 4/1991 | Angerbauer et al. | 514/277 |
| 5,091,378 | 2/1992 | Karanewsky et al. | 514/80 |
| 5,137,881 | 8/1992 | Hübsch et al. | 514/81 |
| 5,169,857 | 12/1992 | Angerbauer et al. | 514/344 |
| 5,177,080 | 1/1993 | Angerbauer et al. | 514/277 |

FOREIGN PATENT DOCUMENTS

| | | |
|---|---|---|
| 0022478 | 1/1981 | European Pat. Off. . |
| 0306929 | 3/1989 | European Pat. Off. . |
| 0325130 | 7/1989 | European Pat. Off. . |

OTHER PUBLICATIONS

J. Med. Chem. 1990, vol. 33, pp. 52–60; "Synthesis and biological activity of new HMG–CoA reductase inhibitors . . . ", G. Beck et al.

Journal of Chromatography, vol. 162 (1979), pp. 281–292; CHROMBIO 275, "Determination of Free, Total, and Esterified Cholesterol by High-Performance Liquid Chromatography", I. W. Duncan et al.

Primary Examiner—C. Warren Ivy
Assistant Examiner—A. A. Owens
Attorney, Agent, or Firm—Sprung Horn Kramer & Woods

[57] ABSTRACT

New substituted pyridines are prepared by reducing suitably substituted pyridine derivatives. The new substituted pyridines are suitable as active compounds in pharmaceuticals, in particular for the treatment of hyperlipoproteinaemia.

11 Claims, No Drawings

SUBSTITUTED PYRIDINES

The invention relates to new substituted pyridines, to a process for their preparation, and to their use in pharmaceuticals.

It has been disclosed that lactone derivatives isolated from fungal cultures are inhibitors of 3-hydroxy-3-methyl-glutaryl coenzyme A reductase (HMG-CoA reductase) [mevinolin, EP 22,478; US 4,231,938].

Furthermore, it has been disclosed that pyridine-substituted dihydroxyheptenoic acids are HMG-CoA reductase inhibitors [EP 325,130; EP 307,342; EP 306,929].

The present invention now relates to new substituted pyridines of the general formula (I)

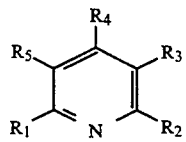

in which $R^1$ represents cycloalkyl having 3 to 7 carbon atoms, or represents straight-chain or branched alkyl having up to 8 carbon atoms, or represents phenyl which is optionally up to disubstituted by identical or different substituents from the series consisting of halogen, trifluoromethyl or straight-chain or branched alkyl having up to 6 carbon atoms, or represents a radical of the formula

in which $R^6$ and $R^7$ are identical or different and denote hydrogen or straight-chain or branched alkyl having up to 4 carbon atoms, $R^2$ represents cycloalkyl-having 3 to 7 carbon atoms, or represents straight-chain or branched alkyl having up to 8 carbon atoms, $R^3$ represents a radical of the formula

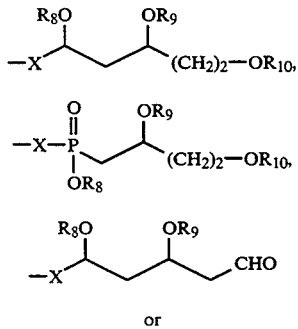

or

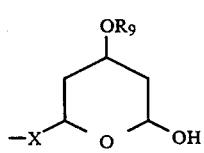

in which

X denotes the group $-CH_2-CH_2-$, $-CH=CH-$ or $-C\equiv C-$, $R^8$, $R^9$ and $R^{10}$ are identical or different and denote hydrogen or a radical of the formula $-CO-R^{11}$ or $-COO-R^{12}$, in which $R^{11}$ and $R^{12}$ are identical or different and denote straight-chain or branched alkyl having up to 8 carbon atoms, or phenyl, or $R^8$ and $R^9$ together form a radical of the formula

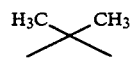

$R^4$ represents phenyl which is optionally up to disubstituted by identical or different substituents from the series consisting of halogen, trifluoromethyl, methoxy, phenoxy or straight-chain or branched alkyl having up to 8 carbon atoms, $R^5$ has the abovementioned meaning of $R^3$ and is identical with, or different from, this meaning, or represents hydrogen, cyano, carboxyl or straight-chain or branched alkoxycarbonyl having up to 8 carbon atoms, or represents straight-chain or branched alkyl having up to 8 carbon atoms which is optionally substituted by halogen, hydroxyl or straight-chain or branched alkoxy having up to 8 carbon atoms or by a group of the formula $-O-(CH_2)_a-R^{13}$ or $-O-CO-R^{14}$, in which a denotes a number 0 or 1, $R^{13}$ denotes phenyl or benzyl, each of which is optionally up to disubstituted by identical or different substituents from the series consisting of halogen, trifluoromethyl, cyano, nitro or straight-chain or branched alkyl having up to 6 carbon atoms, $R^{14}$ has the abovementioned meaning of $R^{13}$ and is identical with, or different from, this meaning, or denotes straight-chain or branched alkyl having up to 8 carbon atoms, or $R^5$ represents a radical of the formula $-CH=N-O-R^{15}$, in which $R^{15}$ has the abovementioned meaning of $R^{14}$ and is identical with, or different from, this meaning.

Depending on the lateral chains mentioned under $R^a$ and/or $R^5$, the compounds according to the invention have in each case 1 or 2 asymmetric carbon atoms to which the radicals $-OR^8$ and $-OR^9$ are bonded. They can therefore exist in various stereochemical forms.

The invention relates to the individual isomers and to the mixtures thereof. Depending on the relative position of the radicals $-OR^8/-OR^9$, the substances according to the invention can be present in the erythro configuration or in the threo configuration. This can be illustrated by way of example for the substituent (a) [$R^3R^5$]:

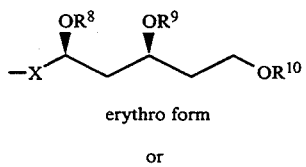

erythro form or

-continued

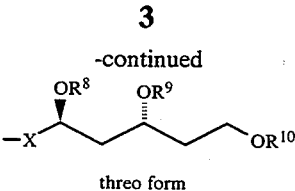

threo form

Two enantiomers exist, in turn, of the substances in the threo and of the substances in the erythro configuration. Due to the double bond (A and B=—CH=CH—), the substances according to the invention can, moreover, exist in the E configuration or the Z configuration. Compounds in the E configuration are preferred.

Moreover, the aldehyde radicals are in each case in an equilibrium with the corresponding pyranes

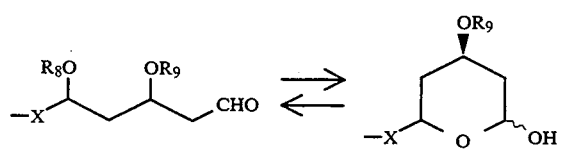

Preferred compounds of the general formula (I) are those
in which $R^1$ represents cyclopropyl, cyclopentyl or straight-chain or branched alkyl having up to 6 carbon atoms, or represents phenyl which is optionally substituted by fluorine, chlorine, trifluoromethyl or methyl, $R^2$ represents cyclopropyl, cyclopentyl or cyclohexyl, or represents straight-chain or branched alkyl having up to 6 carbon atoms, $R^3$ represents a radical of the formula

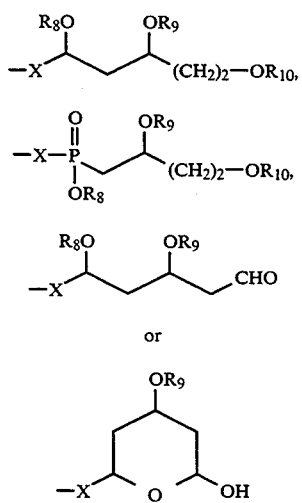

in which

X denotes the group —CH$_2$—CH$_2$—, —CH=CH— or —C≡C—, $R^8$, $R^9$ and $R^{10}$ are identical or different and denote hydrogen or a radical of the formula —CO—$R^{11}$ or —COO—$R^{12}$,
in which $R^{11}$ and $R^{12}$ are identical or different and denote straight-chain or branched alkyl having up to 6 carbon atoms, or phenyl,
or $R^8$ and $R^9$ together form a radical of the formula

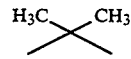

$R^4$ represents phenyl which is optionally up to disubstituted by identical or different substituents from the series consisting of fluorine, chlorine, bromine, trifluoromethyl or straight-chain or branched alkyl having up to 6 carbon atoms, $R^5$ has the abovementioned meaning of $R^3$ and is identical with, or different from, this meaning, or represents hydrogen, cyano, carboxyl or straight-chain or branched alkoxycarbonyl having up to 6 carbon atoms, or represents straight-chain or branched alkyl having up to 6 carbon atoms which is optionally substituted by fluorine, chlorine, bromine, hydroxyl or straight-chain or branched alkoxy having up to 6 carbon atoms, or which is substituted by a group of the formula —O—(CH$_2$)$_a$—$R^{13}$ or —O—CO—$R^{14}$,
in which a denotes 0 or 1, and $R^{13}$ denotes phenyl or benzyl, each of which is optionally substituted by fluorine, chlorine, bromine, trifluoromethyl, cyano, nitro or straight-chain or branched alkyl having up to 4 carbon atoms, $R^{14}$ has the abovementioned meaning of $R^{13}$ and is identical with, or different from, this meaning, or denotes straight-chain or branched alkyl having up to 6 carbon atoms,
or $R^5$ represents a radical of the formula —CH=N—O—$R^{15}$,
in which $R^{15}$ has the abovementioned meaning of $R^{14}$ and is identical with, or different from, this meaning.

Particularly preferred compounds of the general formula (I) are those
in which $R^1$ represents cyclopropyl or straight-chain or branched alkyl having up to 4 carbon atoms, $R^2$ represents cyclopropyl or straight-chain or branched alkyl having up to 4 carbon atoms, $R^3$ represents a radical of the formula

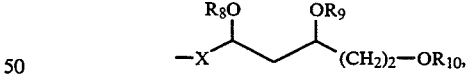

or

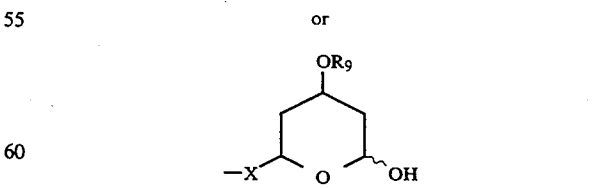

in which

X denotes the group —CH$_2$—CH$_2$—or —CH=CH—, $R^8$, $R^9$ and $R^{10}$ are identical or different and denote hydrogen or a radical of the formula —CO—$R^{11}$,
in which $R^{11}$ denotes straight-chain or branched alkyl having up to 4 carbon atoms, $R^4$ represents phenyl which is optionally substituted by fluorine, trifluoromethyl or by straight-chain or branched alkyl having up to 4 carbon atoms, $R^5$ has the abovementioned meaning of $R^3$ and is identical with, or different from, this meaning, or represents hydrogen or straight-chain or branched alkyl having up to 4 carbon atoms which is optionally substituted by hydroxyl or by straight-chain or branched alkoxy having up to 4 carbon atoms or by p-fluorobenzyloxy.

Very particularly preferred compounds of the general formula (I) are those
in which
$R^1$ represents straight-chain or branched alkyl having up to 4 carbon atoms, $R^2$ represents cyclopropyl or straight-chain or branched alkyl having up to 4 carbon atoms, $R^3$ represents a radical of the formula

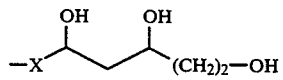

in which
X denotes the group —$CH_2$—$CH_2$—or —CH=CH—, $R^4$ represents phenyl which is optionally substituted by fluorine,
and $R^5$ has the abovementioned meaning of $R^3$ or represents straight-chain or branched alkyl having up to 4 carbon atoms which can optionally be substituted by hydroxyl or alkoxy having up to 4 carbon atoms or by fluorobenzyloxy.

Furthermore, a process for the preparation of the compounds of the general formula (I) according to the invention has been found, which is characterised in that compounds of the general formula (II)

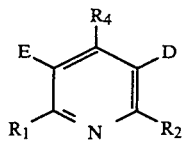

in which
$R^1$, $R^2$ and $R^4$ have the abovementioned meaning and
D represents a radical of the formula

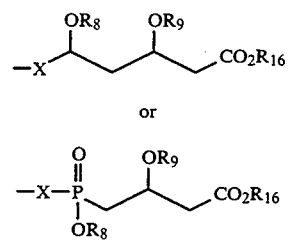

in which
A, B, $R^8$ and $R^9$ have the abovementioned meaning,
$R^{16}$ represents $C_1$-$C_6$-alkyl and
E either also has the abovementioned meaning of D or represents a different substituent mentioned above under $R^3$, are reduced in inert solvents under a protective gas atmosphere, if appropriate via the aldehyde stage, and, in the event that —X—represents the —$CH_2$—$CH_2$—group, the ethene group (X=—CH=CH—) or the ethyne group (X=—C≡C—), are hydrogenated gradually by customary methods and, if appropriate, the isomers are separated.

The process according to the invention can be illustrated by way of example by the following equation:

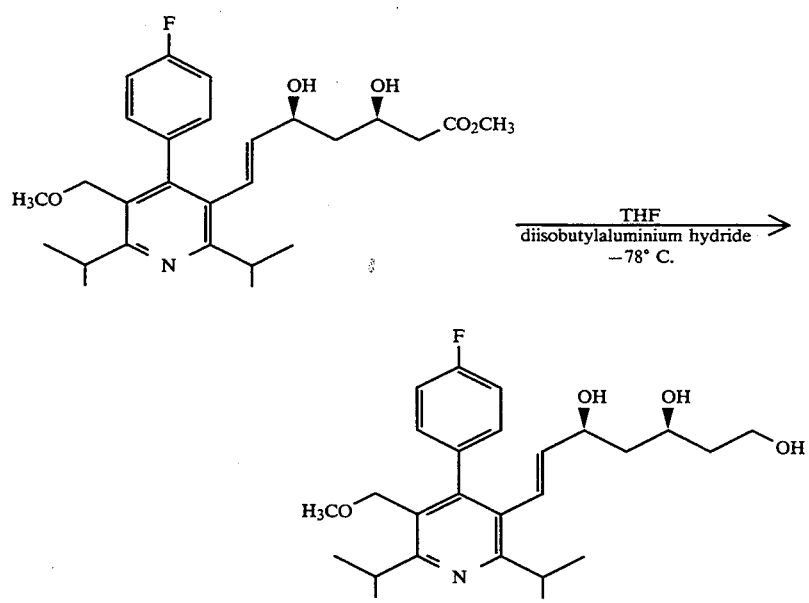

Suitable solvents for the reduction are, in general, the customary organic solvents. Ethers, such as diethyl ether, tetrahydrofuran or dioxane, are preferred. Tetrahydrofuran is particularly preferred.

Suitable reducing agents are complex metal hydrides, such as, for example, lithium aluminium hydride, sodium cyanoborohydride, sodium aluminium hydride, diisobutyl-aluminium hydride or sodium bis-(2-methoxyethoxy)dihydroaluminate. Diisobutylaluminium hydride is preferred.

In general, the reducing agent is employed in an amount of 4 mol to 10 mol, preferably from 4 mol to 5 mol, per mole of the compounds of the general formula (II).

In general, the reduction proceeds in a temperature range from −78° C. to +50° C., preferably from −78° C. to 0° C., particularly preferably at −78° C., in each case depending on the choice of the reducing agent and the solvent.

In general, the reduction proceeds under atmospheric pressure, but the process can also be carried out under elevated or reduced pressure.

In general, cyclisation of the aldehydes to give the corresponding pyranes is effected at room temperature or by heating in an inert organic solvent, if appropriate in the presence of molecular sieve.

Suitable solvents are hydrocarbons, such as benzene, toluene, xylene, mineral oil fractions, or tetralin or diglyme or triglyme. Benzene, toluene or xylene are preferably employed. It is also possible to employ mixtures of the abovementioned solvents. Particularly preferably employed substances are hydrocarbons, in particular toluene, in the presence of molecular sieve.

In general, the cyclisation is effected in a temperature range from −40° C. to +100° C., preferably from −25° C. to +50° C.

The hydrogenation is effected by customary methods using hydrogen in the presence of noble-metal catalysts, such as, for example, Pd/C, Pt/C or Raney nickel, in one of the abovementioned solvents, preferably in alcohols, such as, for example, methanol, ethanol or propanol, in a temperature range from −20° C. to +100° C., preferably from 0° C. to +50° C., under atmospheric pressure or superatmospheric pressure.

If appropriate, the triple or double bond is reduced when the abovementioned ester group is reduced.

In the event that D and/or E represent the radical of the formula

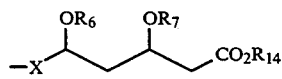

the compounds of the general formula (II) have been disclosed [cf. EP 325,130].

In the event that D and/or E represent the radical of the formula

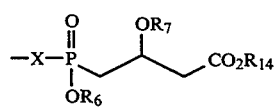

most of the compounds are new. However, they can be prepared analogously to the process published in German Offenlegungsschrift 4,023,308 by reduction, starting from the compounds of the general formula (III)

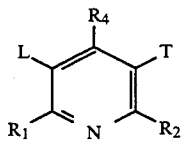

in which

R$^1$, R$^2$ and R$^4$ have the abovementioned meaning
and either L and T, or L or T, represent the radical of the formula

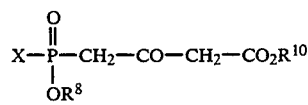

in which

R$^8$ and R$^{10}$ have the abovementioned meaning.

Substances which are particularly suitable as solvents in this case are alcohols, such as methanol, ethanol or propanol, preferably ethanol.

The reduction can be carried out using the customary reducing agents, preferably those which are suitable for reducing ketones to give hydroxy compounds. A reduction with metal hydrides or complex metal hydrides in inert solvents, if appropriate in the presence of a trialkylborane, is particularly suitable for this purpose. The reduction is preferably carried out with complex metal hydrides, such as, for example, lithium borahate, sodium boranate, potassium borahate, zinc borahate, lithium trialkylhydrido-boranate or lithium aluminium hydride. The reduction is particularly preferably carried out using sodium borohydride in the presence of triethylborane.

In general, the reduction proceeds in a temperature range from −78° C. to +50° C., preferably from −78° C. to +25° C., and under atmospheric pressure.

Most of the compounds of the general formula (III) are new and can be prepared analogously to known methods [cf. DE 3,817,298 A; US 5,091,378].

In the case of the enantiomerically pure compounds of the general formula (I), either the corresponding enantiomerically pure esters of the general formula (II) are employed, which can be obtained by published processes [cf. German Offenlegungsschrift 4,040,026] by reaction of the racemic products with enantiomerically pure amines to give the corresponding diastereomeric amide mixtures, followed by a resolution by means of chromatography or crystallisation to give individual diastereomers, followed by hydrolysis, or the racemic end products are resolved by customary chromatographic methods.

The substituted pyridines according to the invention and their isomeric forms have valuable pharmacological properties which are superior compared with the prior art; in particular, they are highly active in vivo as inhibitors of 3-hydroxy-3-methyl-glutaryl coenzyme A (HGM CoA) reductase and thus inhibitors of cholesterol biosynthesis. They can therefore be employed for the treatment of hyperlipoproteinaemia or arteriosclerosis. Moreover, the active compounds according to the invention cause the cholesterol content in the blood to be reduced.

The pharmacological activity of the substances according to the invention was determined in the following assay:

Bioassay for HMG-CoA reductase inhibitors

In the mammalian organism, cholesterol is synthesised from acetate units. In order to measure the hepatic cholesterol biosynthesis in vivo, radio-labelled $^{14}C$ acetate was administered to the animals, and the content of $^{14}C$ cholesterol in the liver was determined at a later point in time.

The test substances were tested in vivo on male Wistar rats having a body weight of between 140 and 160 g for inhibition of the hepatic cholesterol biosynthesis. To this end, the rats were weighed 18 hours before the substances were administered orally, divided into groups of 6 animals each (control group without administration of substance: 8 animals) and starved. Immediately prior to administration, the test substances were suspended in an aqueous, 0.75% strength traganth suspension using an Ultra-Turrax. The traganth suspension (control animals), and the substances suspended in traganth, respectively, were administered by means of tube 2 hours after administering the substance orally, the animals were injected intraperitoneally with $^{14}C$ acetate (12.5 $\mu$Ci/animal).

A further 2 hours later (4 hours after administration of the substance), the animals were sacrificed by cutting their throats and exsanguinated. The peritoneal cavity was subsequently opened, and a liver sample of approx. 700 mg was removed for determining the $^{14}C$ cholesterol which had been synthesised from $^{14}C$ acetate. The cholesterol was extracted by a modified method of Duncan et al. (J. Chromatogr. 162 (1979) 281-292). The liver sample was homogenised in isopropanol in a glass potter. The sample was shaken and subsequently centrifuged, the supernatant was treated with KOH in alcohol, and the cholesterol esters were hydrolysed. After hydrolysis, the total cholesterol was extracted by shaking with heptane, and the supernatant was evaporated. The residue was taken up in isopropanol, and the mixture was transferred into scintillation tubes and made up with LSC cocktail. The $^{14}C$ cholesterol which had been synthesised in the liver from $^{14}C$ acetate was measured in the liquid-scintillation counter. The hepatic $^{14}C$ cholesterol content of the animals which had been treated with traganth only was used as a control. The inhibitory activity of the substances is given as a percentage of the hepatic $^{14}C$ cholesterol content synthesised by the traganth control animals (=100%).

| Example No. | Dosage rate resulting in a 50% inhibition of hepatic $^{14}C$ cholesterol synthesis ($\mu$g/kg of body weight, per oral) |
|---|---|
| 1 | 20 |

The present invention also includes pharmaceutical preparations comprising, in addition to inert, non-toxic, pharmaceutically acceptable auxiliaries and carriers, one or more compounds of the general formula (I), or which are composed of one or more active compounds of the formula (I), and processes for producing these preparations.

These preparations should comprise the active compounds of the formula (I) in a concentration of 0.1 to 99.5% by weight, preferably 0.5 to 95% by weight, of the total mixture.

Besides the active compounds of the formula (I), the pharmaceutical preparations can also comprise other pharmaceutical active compounds.

The pharmaceutical preparations which have been mentioned above can be prepared by known methods in a customary manner, for example using an auxiliary or carrier, or auxiliaries or carriers.

In order to achieve the desired result, it has generally proven advantageous to administer the active compound, or active compounds, of the formula (I) in total amounts of approximately 0.1 $\mu$g/kg up to approximately 100 $\mu$g/kg, preferably in total amounts of approximately 1 $\mu$g/kg to 50 $\mu$g/kg of body weight every 24 hours, if appropriate in the form of several single doses.

However, it may be advantageous to deviate from the abovementioned amounts, depending on the nature and the body weight of the subject treated, on the individual behaviour towards the pharmaceutical, on the nature and severity of the disease, the type of preparation and application, and on the point in time or interval at which the pharmaceutical is administered.

Starting compounds

Example I

Methyl 3R,5S-(+)-erythro-(E)-7-[4-(4-fluorophenyl)-2,6-diisopropyl-5-methoxymethyl-pyrid-3-yl]-3,5-dihydroxy-hept-6-enoate

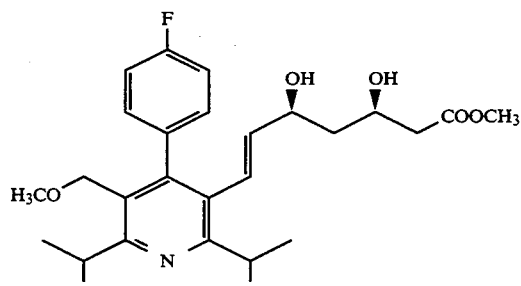

4.81 g (10 mmol) of sodium 3R,5S-(+)-erythro-(E)-7-[4-(4-fluorophenyl)-2,6-diisopropyl-5-methoxymethyl-pyrid-3yl]-3,5-dihydroxy-hept-6-enoate are dissolved in 100 ml of water, and the pH is brought to 4 by adding 1N hydrochloric acid. The mixture is extracted twice using 150 ml of methylene chloride. The organic phase is dried using $Na_2SO_4$ and then reacted with a solution of diazomethane in ether until the reaction is complete. The solvent is subsequently stripped off on a rotary evaporator, and the residue is dried under a high vacuum.

Yield: 4.65 g (98% of theory)

$^1$H NMR (CDCl$_3$): $\delta$=1.23 (m, 6H); 1.32 (d, 6H); 1.40 (m, 2H); 2.43 (m, 2H); 3.18 (s, 3H); 3.32 (m, 2H); 3.73 (s, 3H); 4.05 (s, 2H); 4.08 (m, 1H); 4.29 (m, 1H); 5.23 (dd, 1H); 6.31 (d, 1H); 7.0–7.20 (m, 4H)ppm. Specific rotation (EtOH): $[\alpha]^{20}_D$=41.7° (c=1.0)

Preparation Examples

Example 1

S,5S-(+)-(E)-7-[4-(4-fluorophenyl)-2,6-diisopropyl-5-methoxymethyl-pyrid-3-yl]-hept-6-ene-1,3,5-triol

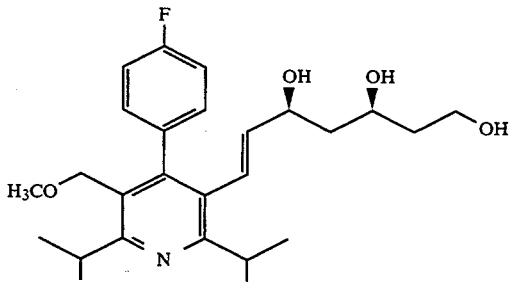

4 g (8.5 mmol) of the compound from Example 1 are dissolved in 100 ml of absolute THF under argon. 35.8 ml (43 mmol) of a 1.2M diisobutylaluminium hydride solution (in toluene) are added dropwise at −78° C. After 12 hours at −30° C., the reaction solution is allowed to come to 0° C., and 150 ml of water are added carefully. The mixture is subsequently extracted 3 times using 200 ml portions of ethyl acetate. The organic phase is washed with saturated NaCl solution, dried with $Na_2SO_4$ and concentrated on a rotary evaporator. After chromatography over silica gel 60 (25–40 μm, eluent ethyl acetate/petroleum ether 7/3), the desired product is obtained.

Yield: 1.98 g (52% of theory)

$^1$H NMR ($CDCl_3$): δ=1.2–1.5 (m, 2H); 1.23 (dd, 6H); 1.36 (d, 6H); 1.65 (m, 2H); 3.19 (s, 3H); 3.30 (m, 2H); 3.82 (m, 2H); 4.02 (m, 1H); 4.07 (s, 2H); 4.27 (m, 1H); 5.26 (dd, 1H); 6.28 (d, 1H); 7.0–7.2 (m, 4H) ppm.

Specific rotation (EtOH): $[α]^{20}_D$=31.1° (c=1.0)

Example 2

3S,5S(+)-(E)-7-[5-(4-fluorobenzyloxymethyl)-4-(4-fluorophenyl)-2,6-diisopropyl-pyrid-3-yl)hept-6-ene-1,3,5-triol

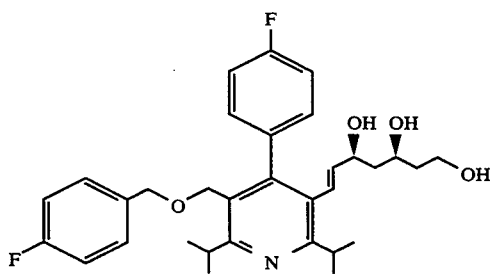

The preparation is carried out analogously to Examples I and 1, using sodium 3R,5S-(+)-erythro-(E)-7-[5-(4-fluorobenzyloxymethyl)-4-(4-fluorophenyl)-2,6-diisopropyl-pyrid-3-yl]-3,5-dihydroxy-hept-6-enoate.

$^1$NMR ($CDCl_3$): δ=1.1–1.4 (m, 2H); 1.18 (dd, 6H); 1.22 (d, 6H); 1.58 (m, 2H); 3.32 (m, 2H); 3.78 (m, 2H); 3.95 (m, 1H); 4.06 (s, 2H); 4.18 (m, 1H); 4.22 (s, 2H); 5.18 (dd, 1H); 6.22 (dd, 1H); 6.8–7.2 (m, 8H) ppm.

Example 3

Erythro (E)-7-[4-(4-fluorophenyl)-5-hydroxymethyl-2,6-diisopropyl-pyrid-3-yl]-hept-6-ene-1,3,5-triol

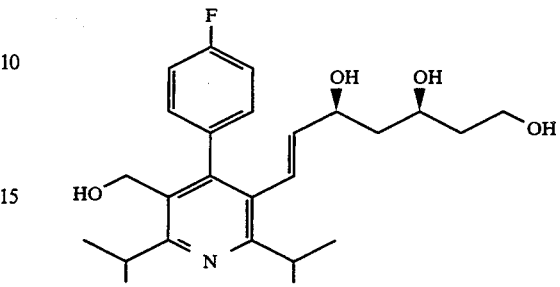

The preparation is carried out analogously to Examples I and 1 starting from sodium erythro-[4-(4-fluorophenyl)-5-hydroxymethyl-2,6-diisopropyl-pyrid-3-yl]-3,5-dihydroxyhept-6-enoate.

$^1$H NMR ($CDCl_3$): δ=1.2–1.4 (m, 2H); 1.22 (dd, 6H); 1.32 (d, 6H); 1.55 (m, 2H); 3.28 (sept., 1H); 3.42 (sept., 1H); 3.86 (m, 2H); 4.03 (m, 1H); 4.28 (m, 1H); 4.42 (d, 2H); 5.27 (dd, 1H); 6.28 (d, 1H); 7.0–7.2 (m, 2H) ppm.

Example 4

2,6-Diisopropyl-4-(4-fluorophenyl)-3,5-bis-(erythro-3,5,7-trihydroxy-hept-1-(E)-enyl)-pyridine

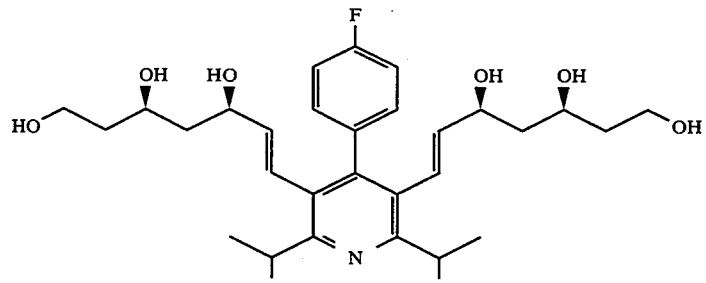

The preparation is carried out analogously to Examples I and 1 starting from 2,6-diisopropyl-4-(4-fluorophenyl)-3,5-bis-(methyl-erythro-(E)-3,5-dihydroxy-hept-6-enoate-7-yl)-pyridine $^1$H NMR ($CDCl_3$) δ=1.2–1.4 (m, 12H); 1.4 - 1.7 (m, 8H); 3.29 (hept. 2H); 3.83 (m, 4H); 4.03 (m, 2H); 4.30 (m, 2H); 5.28 (dd, 2H); 6.28 (d, 2H); 6.9–7.1 (m, 4H) ppm.

Example 5

Erythro-(E)-7- [2-(4-fluorophenyl)-4,6-diisopropyl-5-methoxymethyl-pyrid-3-yl]-hept-6-en-1,3,5-triol

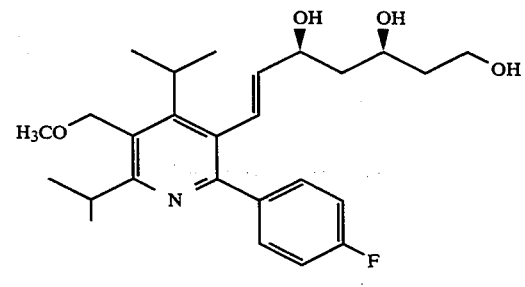

Preparation in analogy to example 1 from methyl-erythro-(E)-7-[2-(4-fluorophenyl)-4,6-diisopropyl-5-methoxymethyl-pyrid-3-yl]-3,5-dihydroxy-hept-6-enoate Yield: 34%, colorless oil
MS (DCI): 446 (30%, M+H)

We claim:

1. New substituted pyridines of the formula

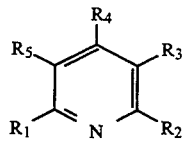 (I)

in which
$R^1$ represents cycloalkyl having 3 to 7 carbon atoms, or represents straight-chain or branched alkyl having up to 8 carbon atoms, or represents phenyl which is optionally up to disubstituted by identical or different substituents selected from the group consisting of halogen, trifluoromethyl and straight-chain or branched alkyl having up to 6 carbon atoms, or represents a radical of the formula

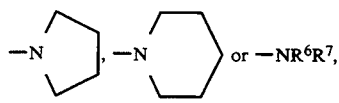

in which
$R^6$ and $R^7$ are identical or different and denote hydrogen or straight-chain or branched alkyl having up to 4 carbon atoms, $R^2$ represents cycloalkyl having 3 to 7 carbon atoms, or represents straight-chain or branched alkyl having up to 8 carbon atoms, $R^3$ represents a radical of the formula

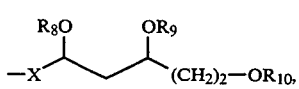 (a)

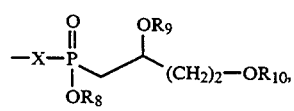 (b)

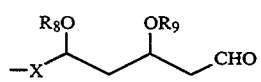 (c)

or

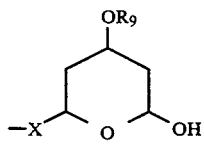 (d)

in which
X denotes the group $-CH_2-CH_2-$, $-CH=CH-$ or $-C\equiv C-$, $R^8$, $R^9$ and $R^{10}$ are identical or different and denote hydrogen or a radical of the formula $-CO-R^{11}$ or $-COO-R^{12}$, in which
$R^{11}$ and $R^{12}$ are identical or different and denote straight-chain or branched alkyl having up to 8 carbon atoms, or phenyl, or $R^8$ and $R^9$ together form a radical of the formula

$R^4$ represents phenyl which os optionally mono- or disubstituted by identical or different substituents selected from the group consisting of halogen, trifluoromethyl, methoxy, phenoxy and straight-chain or branched alkyl having up to 8 carbon atoms, $R^5$ independently has any of the abovementioned meanings of $R^3$, or
represents hydrogen, cyano, carboxyl or straight-chain or branched alkoxycarbonyl having up to 8 carbon atoms, or represents straight-chain or branched alkyl having up to 8 carbon atoms which is optionally substituted by halogen, hydroxyl or straight-chain or branched alkoxy having up to 8 carbon atoms or by a group of the formula $-O-(CH_2)_a-R^{13}$ or $-O-CO-R^{14}$, or a radical of the formula $-CH=N-O-R^{15}$, in which
a denotes a number 0 or 1,
$R^{13}$ denotes phenyl or benzyl, each of which is mono- or disubstituted by identical or different substituents selected from the group consisting of halogen, trifluoromethyl, cyano, nitro and straight-chain or branched alkyl having up to 6 carbon atoms, and
$R^{14}$ and $R^{15}$ each has any of the abovementioned meaning of $R^{13}$, or denotes straight-chain or branched alkyl having up to 8 carbon atoms.

2. New substituted pyridines according to claim 1
in which
$R^1$ represents cyclopropyl, cyclopentyl or straight-chain or branched alkyl having up to 6 carbon atoms, or represents phenyl which is optionally substituted by fluorine, chlorine, trifluoromethyl or methyl, $R^2$ represents cyclopropyl, cyclopentyl or cyclohexyl, or represents straight-chain or branched alkyl having up to 6 carbon atoms, $R^3$ represents a radical of the formula

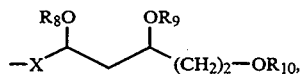

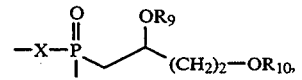

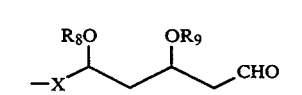

or

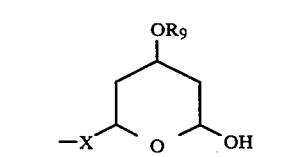

in which
X denotes the group $-CH_2-CH_2-$, $-CH=CH-$ or $-C\equiv C-$, $R^8$, $R^9$ and $R^{10}$ are identical or different and denote hydrogen or a radical of the formula $-CO-R^{11}$ or $-COO-R^{12}$, in which
$R^{11}$ and $R^{12}$ are identical or different and denote straight-chain or branched alkyl having up to 6 carbon atoms, or phenyl,
or
$R^8$ and $R^9$ together form a radical of the formula

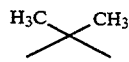

$R^4$ represents phenyl which is optionally mono- or di-substituted by identical or different substituents selected from the group consisting of fluorine, chlorine, bromine, trifluoromethyl and straight-chain or branched alkyl having up to 6 carbon atoms, $R^5$ independently has any of the abovementioned meanings of $R^3$, or represents hydrogen, cyano, carboxyl or straight-chain or branched alkoxycarbonyl having up to 6 carbon atoms, or represents straight-chain or branched alkyl having up to 6 carbon atoms which is optionally substituted by fluorine, chlorine, bromine, hydroxyl or straight-chain or branched alkoxy having up to 6 carbon atoms, or which is substituted by a group of the formula —O—(CH$_2$)$_a$—R$^{13}$ or —O—CO—R$^{14}$, or represents a radical of the formula —CH=N—O—R$^{15}$, in which a denotes 0 or 1, and $R^{13}$ denotes phenyl or benzyl, each of which is optionally substituted by fluorine, chlorine, bromine, trifluoromethyl, cyano, nitro or straight-chain or branched alkyl having up to 4 carbon atoms, and $R^{14}$ and $R^{15}$ each has any of the abovementioned meanings of $R^{13}$, or denotes straight-chain or branched alkyl having up to 6 carbon atoms.

3. New substituted pyridines according to claim 1 in which $R^1$ represents cyclopropyl or straight-chain or branched alkyl having up to 4 carbon atoms, $R^2$ represents cyclopropyl or straight-chain or branched alkyl having up to 4 carbon atoms, $R^3$ represents a radical of the formula

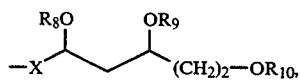

or

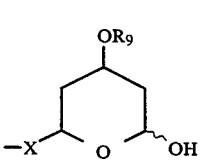

in which

X denotes the group —CH$_2$—CH$_2$— or —CH=CH—, $R^8$, $R^9$ and $R^{10}$ are identical or different and denote hydrogen or a radical of the formula —CO—R$^{11}$, in which $R^{11}$ denotes straight-chain or branched alkyl having up to 4 carbon atoms, $R^4$ represents phenyl which is optionally substituted by fluorine, trifluoromethyl or by straight-chain or branched alkyl having up to 4 carbon atoms, $R^5$ independently has any of the abovementioned meanings of $R^3$, or represents hydrogen or straight-chain or branched alkyl having up to 4 arbona toms which is optionally substituted by hydroxyl or by straight-chain or branched alkoxy having up to 4 carbon atoms or by p-fluorobenzyloxy.

4. New substituted pyridines according to claim 1 in which $R^1$ represents straight-chain or branched alkyl having up to 4 carbon atoms, $R^2$ represents cyclopropyl or straight-chain or branched alkyl having up to 4 carbon atoms, $R^3$ represents a radical of the formula

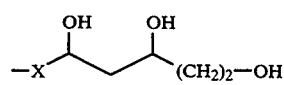

in which

X denotes the group —CH$_2$—CH$_2$— or —CH=CH—, $R^4$ represents phenyl which is optionally substituted by fluorine, and $R^5$ has the abovementioned meaning of $R^3$ or represents straight-chain or branched alkyl having up to 4 carbon atoms which can optionally be substituted by hydroxyl or alkoxy having up to 4 carbon atoms or by p-fluorobenzyloxy.

5. A compound according to claim 1 wherein such compound is 3S,5S-(+)-(E)-7-[4-(4-fluorophenyl)-2,6-diisopropyl-5-methoxymethyl-pyrid-3-yl]-hept-6-ene-1,3,5-triol of the formula

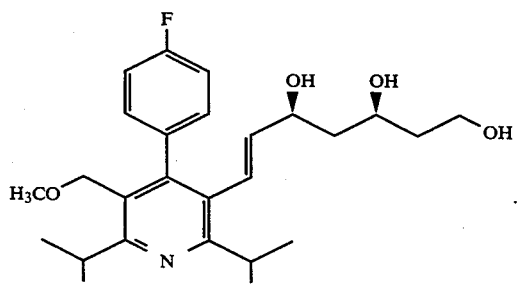

6. A compound according to claim 1 wherein such compound is 3S, 5S (+)-(E)-7-[5-(4-fluorobenzyloxymethyl)-4-(4-fluorophenyl)-2,6-diisopropyl-pyrid-3 yl)hept-6-ene-1,3,5-triol of the formula

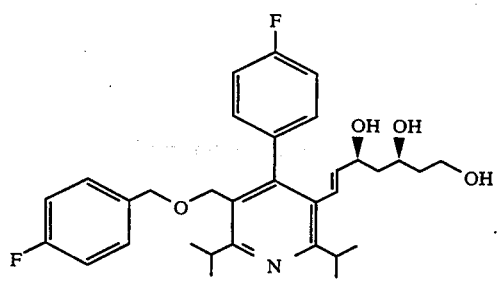

7. A compound according to claim 1 wherein such compound is Erythro (E)-7-[4-(4-fluorophenyl)-5-hydroxymethyl-2,6-diisopropyl-pyrid-3-yl]-hept-6-ene-1,3,5-triol of the formula

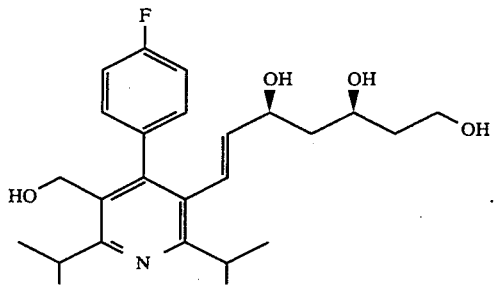

8. A compound according to claim 1 wherein such compound is 2,6-Diisopropyl-4-(4-fluorophenyl)-3,5-bis-(erythro-3,5,7-trihydroxy-hept-1-(E)-enyl)-pyridine of the formula

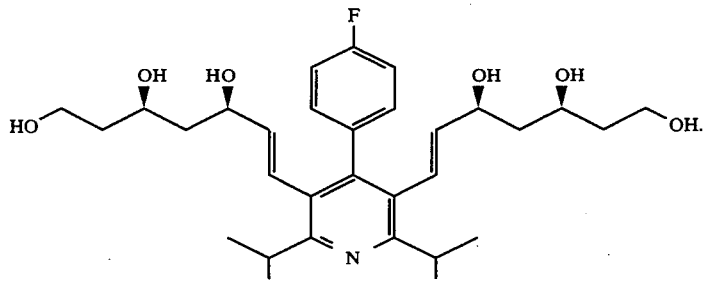

9. A composition for the treatment of hyperlipoproteinaemie and arteriosclerosis comprising an amount effective therefor of a compound or salt thereof according to claim 1 and a pharmacologically acceptable diluent.

10. A method of treating hyperlipoproteinaemia and arteriosclerosis in a patient in need thereof which comprises administering to such patient an amount effective therefor of a compound or salt thereof according to claim 1.

11. The method according to claim 10, wherein such compound is
3S,5S-(+)-(E)-7-[4-(4-fluorophenyl)-2,6-diisopropyl-5-methoxymethyl-pyrid-3-yl]-hept-6-ene-1,3,5-triol,
3S,5S(+)-(E)-7-[5-(4-fluorobenzyloxymethyl)-4-(4-fluorophenyl)-2,6-diisopropyl-pyrid-3-yl)hept-6-ene-1,3,5-triol,
Erythro (E)-7-[4-(4-fluorophenyl)-5-hydroxymethyl-2,6-diisopropyl-pyrid-3-yl]-hept-6-ene-1,3,5-triol, or
2,6-Diisopropyl-4-(4-fluorophenyl)-3,5-bis-(erythro-3,5,7-trihydroxy-hept-1-(E)-enyl)-pyridine, or a salt thereof.

* * * * *